US009474732B2

(12) United States Patent
Prentice et al.

(10) Patent No.: US 9,474,732 B2
(45) Date of Patent: *Oct. 25, 2016

(54) INTRATHECAL BACLOFEN PHARMACEUTICAL DOSAGE FORMS WITH FEWER DEGRADATION PRODUCTS

(71) Applicant: Mallinckrodt LLC, Hazelwood, MO (US)

(72) Inventors: Thomas R. Prentice, Lake Elmo, MN (US); Angela A. Strantz, Mahtomedi, MN (US)

(73) Assignee: Mallinckrodt LLC, Hazelwood, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/574,733

(22) Filed: Dec. 18, 2014

(65) Prior Publication Data

US 2015/0105466 A1   Apr. 16, 2015

Related U.S. Application Data

(63) Continuation of application No. 12/701,342, filed on Feb. 5, 2010, now Pat. No. 8,969,414.

(60) Provisional application No. 61/150,337, filed on Feb. 6, 2009.

(51) Int. Cl.
*A61K 31/197* (2006.01)
*A61K 31/4015* (2006.01)
*A61K 31/195* (2006.01)
*A61K 9/00* (2006.01)

(52) U.S. Cl.
CPC ........... *A61K 31/197* (2013.01); *A61K 9/0085* (2013.01); *A61K 31/195* (2013.01); *A61K 31/4015* (2013.01); *A61K 9/0019* (2013.01); *Y10S 514/906* (2013.01)

(58) Field of Classification Search
None
See application file for complete search history.

(56) References Cited

U.S. PATENT DOCUMENTS

| 5,149,713 | A | 9/1992 | Bousquet |
| 5,256,154 | A | 10/1993 | Liebert |
| 5,980,927 | A | 11/1999 | Nelson |
| 6,380,176 | B2 | 4/2002 | Takahashi |
| 6,629,954 | B1 | 10/2003 | Heruth |
| 6,754,536 | B2 | 6/2004 | Swoyer |
| 6,969,383 | B2 | 11/2005 | Hildebrand |
| 7,824,697 | B2 | 11/2010 | Trissel |
| 7,998,120 | B2 | 8/2011 | Sano |
| 8,062,647 | B2 | 11/2011 | Trissel |
| 8,083,722 | B2 | 12/2011 | McKay |
| 8,357,379 | B2 | 1/2013 | Trissel |
| 8,529,916 | B2 | 9/2013 | Trissel |
| 8,969,414 | B2 * | 3/2015 | Foster |
| 2001/0051618 | A1 | 12/2001 | Takahashi |
| 2004/0062819 | A1 | 4/2004 | Hildebrand |
| 2004/0220545 | A1 | 11/2004 | Heruth |
| 2004/0267194 | A1 | 12/2004 | Sano |
| 2005/0004219 | A1 | 1/2005 | Hildebrand |
| 2005/0090554 | A1 | 4/2005 | Devane |
| 2005/0244503 | A1 | 11/2005 | Rabinow |
| 2006/0009523 | A1 * | 1/2006 | Trissel |
| 2006/0084925 | A1 | 4/2006 | Ramsahoye |
| 2006/0142396 | A1 | 6/2006 | Meythaler |
| 2010/0056989 | A1 | 3/2010 | McKay |
| 2010/0106097 | A1 | 4/2010 | Elmouelhi |
| 2011/0269836 | A1 | 11/2011 | Foster |
| 2013/0331451 | A1 | 12/2013 | Trissel |
| 2015/0258279 | A1 | 9/2015 | Foster |

FOREIGN PATENT DOCUMENTS

| EP | 2548594 A1 | 1/2013 |
| JP | 53-253022 | 10/1988 |
| WO | 02085428 | 10/2002 |
| WO | 2006017235 | 2/2006 |
| WO | 2010090765 A3 | 8/2010 |

OTHER PUBLICATIONS

Health Canada, "Process Validation: Moist Heat Sterilization for Pharmaceuticals", 2002, pp. 1-15 of 15, downloaded on Jan. 10, 2016 from www.hc-sc.gc.ca/dhp-mps/compli-conform/gmp-bpf/validation/mhsp-schpp-eng.php.*
Medtronic, "LIORESAL® INTRATHECAL" (baclofen injection) product information, Medtronic, Inc., Aug. 2007, downloaded from "www.pdr3d.com" on Sep. 5, 2012, pp. 1-14 of 14.*
Declaration of Thomas R. Prentice Under 37 C.F.R. 1.132, filed in U.S. Appl. No. 12/701,342 on Mar. 15, 2013, 3 pages.*
Sigg, Solubility and Stability of Intrathecal Baclofen Solutions at High Concentrations: Implications for Chronic Use in the SynchroMed Infusion System, White Paper, 2007, Medtronic Neurological, 13 pages.
International Search Report and Written Opinion dated Oct. 4, 2010 from related International application No. PCT/US2010/000352, 7 pgs.
Godwin, Stability of a Baclofen and Clonidine Hydrochloride Admixture for Intrathecal Administration, Hospital Pharmacy, 2001, vol. 36, No. 9, pp. 950-954.
Sitaram, Stability and compatibility of intrathecal admixtures containing baclofen and high concentrations of morphine, Int. J. Pharm., Jul. 1, 1997, vol. 153, Issue 1, pp. 13-24.
Cutrignelli, Comparative effects of some hydrophilic excipients on the rate of gabapentin and baclofen lactamization in lyophilized formulations, Int. J. Pharm., Mar. 2007, vol. 332, Issue 1-2, pp. 98-106.
Center for Drug Evaluation and Research, Guidance for Industry and Review Staff, Nonclinical Safety Evaluation of Reformulated Drug Products and Products Intended for Administration by an Alternate Route, Pharmacology/Toxicology, Mar. 2008, pp. 1-8.
U.S. Pharmacopeia <161> Transfusion and Infusion assemblies and Similar Medical Devices, available at http://www.pharmacopeia.cn/v29240/usp29nf24s)_c161.html; downloaded Apr. 18, 2014, 2 pgs.

(Continued)

*Primary Examiner* — James D Anderson
*Assistant Examiner* — Gregg Polansky

(57) ABSTRACT

The present invention relates generally to a sterile, particulate-free, stable intrathecal baclofen solution with less than 0.5% of 4-(4-chlorophenyl)-2-pyrrolidone, a degradation product. These solutions are stable under a variety of storage conditions and for extended periods of time. Also disclosed are methods for preparing such compositions.

14 Claims, No Drawings

(56) References Cited

OTHER PUBLICATIONS

Orange Book entry for Lioresal. Accessed at <http://www.accessdata.fda.gov/scripts/cder/ob/docs/obdetail.cfm?Appln_No=022462&TABLE1=OB_Rx> downloaded Jul. 29, 2011, 2 pgs.
About Gablofen Common Questions Accessed at <http://www.gablofen.com/common-questions.pho> downloaded Jul. 29, 2011, 3 pgs.
Baclofen; AHFS Drug Information 2003, Baclofen, 1314-1318.
Allen, Stability of baclofen, captopril, dilitiazem hydrochloride, dipyridamole, and flecainide acetate in extemporaneously compounded oral liquids, American Journal of Health System Pharmacy, 1996, 53, 2179-84.
Cruaud, The characterization and release kinetics evaluation of baclofen microspheres designed for intrathecal Injection, International Journal of Pharmaceutics, 1999, 177, 274-257.
Johnson, Stability of an extemporaneously compounded baclofen oral liquid, American Journal of hospital Pharmacy, 1993, 50, 2353-5.
Lioresal Package Insert; Medtronic, Inc., 2003, 2 pgs.
Medtronic Bar Code; Medtronic, Inc., Use by Date Apr. 070, 2010, 1 pg.
Medtronic Instructions for Use; Medtronic, Inc., 2003, 20 pgs.
Medtronic Labels; Medtronic, Inc., Use by Date Mar. 31, 2011, 5 pgs.
Medtronic Product Pics; Medtronic, Inc., pp. 528-548.
Seed, Silanizing Glassware, Current Protocols in Immunology, 1997, Supplement 21, Appendix 3K Basic Protocol, 2 pgs.
Non-final Office action from U.S. Appl. No. 12/403,190 dated Aug. 9, 2011, 11 pgs.
Final Office action from U.S. Appl. No. 12/403,190 dated Apr. 23, 2011, 11 pgs.
Non-final Office action from U.S. Appl. No. 12/403,190 dated May 17, 2013, 10 pgs.
Final Office action from U.S. Appl. No. 12/403,190 dated Jan. 22, 2014, 11 pgs.
Non-final Office action from U.S. Appl. No. 12/403,190 dated Oct. 8, 2014, 13 pgs.
Holloway, "Systemic Pharmacomodulation of Transient Lower Esophageal Sphincter Relations," Amer. J. Medicine, 2001, vol. 111(8A), pp. 178S-185S.
Baum, "Production and Testing of Baclofen Solutions," Pharmazeutische Zeitung, 1988, vol. 133, pp. 2832, Germany (English Abstract).
Ridley, "Intrathecal Baclofen Therapy: Ten Steps Towerd Best Practice," Journal of Neuroscience Nursing, 2006, 38:2, pp. 72-82.
Cardiff, "Concentrating on Baclofen," Australian Journal of Hospital Pharmacy, Feb. 1995, vol. 25, No. 1, pp. 102-103 (abstract).
U.S. Department of Health and Human Services Food and Drug Administration, "Guidance for Industry: Container Closure Systems for Packaging Human Drugs and Biologics", May 1999, pp. 23-25.
Moberg-Wolf, "Potential clinical impact of compounded versus noncompounded intrathecal baclofen," Archives of Physical Medicine and Rehabilitation, Nov. 2009, vol. 90, Issue 11, pp. 1815-1820.
Ahuja, "Baclofen," Analytical Profiles of Drug Substances, 1985, vol. 14, pp. 528-548.
Gupta, "Quantiation of 4-(4-chlorophenyl)-2-Pyrrolidine in vaclofen powder and tablets," Drug Develop. Indust. Pharm., 1988 vol. 14, pp. 1623-1628.
Final Office action from U.S. Appl. No. 12/403,190 dated Mar. 6, 2015, 13 pgs.
Office action from EP Application 11006015.9 dated Aug. 7, 2015, 3 pgs.
Partial European Search Report from EP Application 11006015.9 dated Mar. 16, 2012, 5 pgs.
European Search Report from EP Application 11006015.9 dated Jul. 3, 2012, 8 pgs.

\* cited by examiner

INTRATHECAL BACLOFEN PHARMACEUTICAL DOSAGE FORMS WITH FEWER DEGRADATION PRODUCTS

This application is a continuation application of U.S. patent application Ser. No. 12/701,342, filed Feb. 5, 2010, which claims the benefit of priority of U.S. provisional application No. 61/150,337, filed Feb. 6, 2009, the disclosures of which are hereby incorporated by reference in their entirety.

The present invention relates generally to a sterile, particulate-free, stable intrathecal baclofen solution with less than 0.5% of 4-(4-chlorophenyl)-2-pyrrolidone, a primary degradation product.

Baclofen is a skeletal muscle relaxant and antispastic agent used in the management of severe spasticity of spinal cord and cerebral origin. Baclofen is a structural analog of the inhibitory neurotransmitter gamma-aminobutyric acid (GABA), and may exert its effects by stimulation of the $GABA_B$ receptor subtype. Baclofen is the generic (USAN) name (USP Dictionary of USAN and International Drug Names 2003) for 4-amino-3-(p-chlorophenyl) butyric acid, a derivative of γ-aminobutyric acid. Its structural formula is:

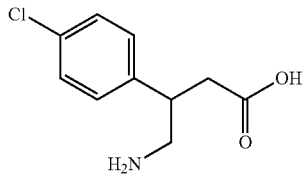 [SMILES: NCC(CC(=O)O)c1ccc(Cl)cc1]

Baclofen is a white to off-white, odorless or practically odorless crystalline powder, with a molecular weight of 213.66 g/mol. It is slightly soluble in water, very slightly soluble in methanol, and insoluble in chloroform.

Baclofen can be administered orally, but when injected directly into the intrathecal space of a patient effective CSF concentrations are achieved with resultant plasma concentrations 100 times less than those occurring with oral administration. Baclofen injections (Lioresal Intrathecal, Medtronic) are therefore commonly administered intrathecally via an implanted pump to manage severe spasticity of spinal cord origin. Presently, intrathecal baclofen is commercially available for injection in 0.5 mg/ml and 2.0 mg/ml solutions having a pH of 5 to 7 in the following simple preservative-free formula (Lioresal Intrathecal package insert):

| | |
|---|---|
| Baclofen | 2 mg |
| Sodium Chloride | 9 mg |
| Water for Injection | qs 1 mL |

The available 0.05 mg, 0.5 mg, and 2 mg/mL concentrations of Lioresal are adequate for many, but not all patient needs. Specifically, when daily dose requirements exceed 0.5 mg/day, pump refill intervals can be as short as 30 days, depending on the size of the implanted pump reservoir. For the majority of the patients receiving intrathecal Baclofen therapy at an average dose of 0.5 mg/day, refill periods are between 60 and 80 days when a standard 20 mL pump is used with the 2 mg/mL concentration. By way of a higher concentration and slower rate of solution delivery, the 4 mg/mL concentration will provide a means of administering currently approved therapeutic doses of intrathecal Baclofen in a manner that reduces the frequency of invasive pump refill procedures and results in improved patient convenience and satisfaction. Moreover, since bacteriological contamination, serious infection, programming errors and/or mixing errors could occur during the refilling process, the reduced frequency of refilling associated with the 4 mg/mL concentration is appealing from a safety perspective. Additionally, the availability of a 4 mg/mL concentration will obviate the need to procure this concentration from compounding pharmacies, a practice that is believed to be increasing due to the non-availability of a baclofen product with a concentration in excess of 2 mg/mL.

While there are no absolute FDA standards for sterilization processes, pharmaceutical solutions are most commonly sterilized using a heating regimen at 121.1° C. with an $F_0$ of about 30 minutes. While this may be an effective method for thermally stable compounds, this practice is counterproductive for some heat-sensitive active pharmaceutical ingredients (APIs). In these cases, the resulting solution may be sterile, but it is often plagued with an unacceptable increase in degradation products brought on by the excessive use of heat in the sterilization process. Furthermore, compositions containing heat-sensitive APIs are often not terminally sterilized to avoid this degradation. Therefore, it is desirable to find and implement a sterilization method that utilizes less harsh conditions in order to prevent this thermal degradation from taking place, while continuing to meet sterility standards.

Indeed, during the dissolution and sterilization process, some baclofen degrades to 4-(4-chlorophenyl)-2-pyrrolidone (4-CPP). This obviously reduces the amount of baclofen in solution, and thus the overall efficacy of the solution. Additionally, this degradation product may have undesirable side effects, including toxicity. The amount of 4-CPP found in commercially available Lioresal is shown in the table below.

| Lioresal (Medtronic) | | | |
|---|---|---|---|
| 0.5 mg/mL | | 2.0 mg/mL | |
| µg/mL 4-CPP | % 4-CPP | µg/mL 4-CPP | % 4-CPP |
| 2.93 | 0.6 | 12.23 | 0.6 |
| 2.92 | 0.6 | 11.98 | 0.6 |
| 2.94 | 0.6 | 12.25 | 0.6 |

Common sterilization protocols call for heating the solution to 121.1° C. with $F_0$ is about 30 minutes. It was hypothesized that shorter heating times may lead to a solution with fewer degradation products, as the baclofen would have less time under the stress of heating to degrade. However, it was unknown if the shorter heating times would lead to a sterile product.

Therefore, there appears to be a clinical need for sterile aqueous solutions of baclofen having fewer degradation products, preferably for concentrated solutions that are also stable in a variety of storage conditions for extended periods of time. Investigations towards these ends have been previously undertaken, without success (Sigg, J. et al., Solubility and Stability of Intrathecal Baclofen Solutions at High Concentrations: Implications for Chronic Use in the SynchroMed Infusion System. White Paper 2007, Minneapolis: Medtronic Neurological: 2007). Due to the heat sensitivity of baclofen product, a product-specific design approach is herein disclosed for the validation of the terminal sterilization cycle as opposed to the standard overkill methodology.

Disclosed herein is an intrathecal baclofen solution with less than 0.5% of 4-(4-chlorophenyl)-2-pyrrolidone, a degradation product, which is at least a 20% decrease versus previous formulations.

According to another aspect, the solution disclosed herein further comprises sodium chloride and sterile water.

According to one aspect, the solution described herein is sterile.

According to another aspect, the solution described herein is free of particulates.

According to yet another aspect, the solution described herein is stable at 25° C. and 60% relative humidity for at least 2 years.

According to a further aspect, the solution described herein is stable at 40° C. and 75% relative humidity for at least 2 years.

According to another aspect, the solution described herein is suitable for intrathecal delivery.

As used herein, the terms below have the meanings indicated.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "sterile," as used herein, means free from all live bacteria or other microorganisms and their spores.

The term "particulate," as used herein, is meant to describe mobile undissolved particles, other than gas bubbles, unintentionally present in the drug solution.

The term "intrathecal," as used herein, means introduced into or occurring in the space under the arachnoid membrane which covers the brain and spinal cord.

The term "stable," as used herein, is meant to describe a compound, composition, or other substance that retains its properties without loss of potency and maintains its physical characteristics over time with minimal degradation. It is expected that the currently disclosed pharmaceutical compositions should be stable for at least two years.

From the foregoing description, one skilled in the art can easily ascertain the essential characteristics of this invention, and without departing from the spirit and scope thereof, can make various changes and modifications of the invention to adapt it to various usages and conditions.

Certain embodiments disclosed herein may be illustrated by the following non-limiting examples.

EXAMPLE 1

Preparation of 4.0 mg/mL Baclofen Solution

To 1 L of hot water is added 630.0 g sodium chloride, and the mixture is stirred for 10±2 minutes. To the resulting solution is added 280.0 g baclofen and 2 L hot water. The mixture is then stirred for 45 minutes. The resulting solution is diluted to 70 L with hot water and stirred for at least an additional 10 minutes.

EXAMPLE 2

Preparation of 2.0 mg/mL Baclofen Solution

To 1 L of hot water is added 315.0 g sodium chloride, and the mixture is stirred for 10±2 minutes. To the resulting solution is added 140.0 g baclofen and 2 L hot water. The mixture is then stirred for 45 minutes. The resulting solution is diluted to 70 L with hot water and stirred for at least an additional 10 minutes.

EXAMPLE 3

Preparation of 0.5 Baclofen Solution

To 1 L of hot water is added 7875 g sodium chloride, and the mixture is stirred for 10±2 minutes. To the resulting solution is added 35.0 g baclofen and 2 L hot water. The mixture is then stirred for 45 minutes. The resulting solution is diluted to 70 L with hot water and stirred for at least an additional 10 minutes.

EXAMPLE 4

Sterilization Protocol

A baclofen solution described herein is aseptically filled in vials. The vials containing the solution are then steam-heated to 121.1° C. so that the $F_0$ for the resulting terminally sterilized solution is 7 minutes.

EXAMPLE 5

Percent 4-CPP Found in Baclofen Solutions

The percent of 4-CPP found in solutions produced via the method disclosed in Examples 1 and 3 are shown below. The degradation to 4-CPP was measured following the storage of aliquots of the solutions at both 25° C. and 60% relative humidity, and 40° C. and 75% relative humidly.

| 0.5 mg/mL | | | |
| --- | --- | --- | --- |
| Lot # | Initial % 4-CPP | 1 month | 2 months |
| 25° C./60% RH | | | |
| 2118-101 | 0.346 | 0.358 | 0.359 |
| 2118-102 | 0.436 | 0.437 | 0.435 |
| 2118-103 | 0.39 | 0.4 | 0.397 |
| Average | 0.391 | 0.398 | 0.397 |
| 40° C./75% RH | | | |
| 2118-101 | 0.346 | 0.392 | 0.402 |
| 2118-102 | 0.436 | 0.438 | 0.481 |
| 2118-103 | 0.39 | 0.412 | 0.454 |
| Average | 0.391 | 0.414 | 0.446 |

| 4.0 mg/mL | | | |
| --- | --- | --- | --- |
| Lot # | Initial % 4-CPP | 1 month | 2 months |
| 25° C./60% RH | | | |
| 2133-101 | 0.377 | 0.394 | 0.382 |
| 2133-102 | 0.415 | 0.429 | 0.429 |
| 2137-101 | 0.442 | 0.447 | 0.456 |
| Average | 0.411 | 0.423 | 0.422 |
| 40° C./75% RH | | | |
| 2133-101 | 0.377 | 0.398 | 0.425 |
| 2133-102 | 0.415 | 0.442 | 0.464 |
| 2137-101 | 0.442 | 0.451 | 0.479 |
| Average | 0.411 | 0.430 | 0.456 |

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A sterile aqueous solution of baclofen sterilized by steam heating and containing 0.5% or less (by weight of baclofen) of 4-(4-chlorophenyl)-2-pyrrolidone, wherein baclofen in the solution is at a concentration from about 0.5 mg/mL to about 4.0 mg/mL.

2. The solution of claim 1, further comprising sodium chloride.

3. The solution of claim 1, wherein the solution contains 0.5% or less (by weight of baclofen) of 4-(4-chlorophenyl)-2-pyrrolidone after storage at 25° C. and 60% relative humidity for at least one year.

4. The solution of claim 1, wherein the solution contains 0.5% or less (by weight of baclofen) of 4-(4-chlorophenyl)-2-pyrrolidone after storage at 40° C. and 75% relative humidity for at least two months.

5. The solution of claim 1, wherein the baclofen concentration is from about 0.5 mg/mL to about 1.0 mg/mL.

6. The solution of claim 1, wherein the baclofen concentration is from about 1.0 mg/mL to about 2.0 mg/mL.

7. The solution of claim 1, wherein the baclofen concentration is from about 2.0 mg/mL to about 3.0 mg/mL.

8. The solution of claim 1, wherein the baclofen concentration is from about 3.0 mg/mL to about 4.0 mg/mL.

9. The solution of claim 1, wherein the solution is suitable for intrathecal delivery.

10. The solution of claim 1, wherein the solution is free of particulates.

11. The solution of claim 1, wherein the steam heating comprises heating the solution to 121.1° C. for a $F_0$ value of 7 minutes.

12. A vial containing the solution of claim 1.

13. The vial of claim 12, wherein the solution contains 0.5% or less (by weight of baclofen) of 4-(4-chlorophenyl)-2-pyrrolidone after storage at 25° C. and 60% relative humidity for at least one year.

14. The vial of claim 12, wherein the solution contains 0.5% or less (by weight of baclofen) of 4-(4-chlorophenyl)-2-pyrrolidone after storage at 40° C. and 75% relative humidity for at least two months.

* * * * *